(12) United States Patent
Gale et al.

(10) Patent No.: US 9,813,078 B2
(45) Date of Patent: Nov. 7, 2017

(54) SYSTEMS AND METHODS FOR AUTOMATED ELECTRICAL ELEMENT ADDRESSING

(71) Applicant: THE CLEVELAND CLINIC FOUNDATION, Cleveland, OH (US)

(72) Inventors: John T. Gale, Chardon, OH (US); Jorge Gonzalez-Martinez, University Hts., OH (US); Imad Najm, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/299,615

(22) Filed: Oct. 21, 2016

(65) Prior Publication Data
US 2017/0117916 A1 Apr. 27, 2017

Related U.S. Application Data

(60) Provisional application No. 62/245,449, filed on Oct. 23, 2015, provisional application No. 62/337,938, filed on May 18, 2016.

(51) Int. Cl.
*A61B 5/04* (2006.01)
*H03M 7/30* (2006.01)
*G06K 19/06* (2006.01)
*A61B 5/00* (2006.01)
*A61B 5/0408* (2006.01)

(52) U.S. Cl.
CPC ............. *H03M 7/30* (2013.01); *G06K 19/06* (2013.01); *A61B 5/0002* (2013.01); *A61B 5/04085* (2013.01); *A61B 5/4362* (2013.01)

(58) Field of Classification Search
CPC .. A61B 5/0002; A61B 5/04085; A61B 5/4362
USPC ............................ 341/51; 600/511, 382, 301
See application file for complete search history.

(56) References Cited

U.S. PATENT DOCUMENTS

| | | | |
|---|---|---|---|
| 5,394,388 A | 2/1995 | Hatanaka et al. | |
| 6,459,392 B1 | 10/2002 | Haggar et al. | |
| 2009/0259133 A1* | 10/2009 | Wolfberg et al. | A61B 5/4362 600/511 |

(Continued)

FOREIGN PATENT DOCUMENTS

KR 20090113208 A 10/2009

OTHER PUBLICATIONS

International Search Report and Written Opinion for corresponding PCT/US2016/058038, dated Feb. 1, 2017, pp. 1-11.

*Primary Examiner* — Joseph Lauture
(74) *Attorney, Agent, or Firm* — Tarolli, Sundheim, Covell & Tummino LLP (57) ABSTRACT

The present disclosure relates generally to automating the task of assignment of labels to identify electrical elements (e.g., electrode contacts, electrodes including a plurality of electrode contacts, and/or non-addressable electrical elements, like wires). A system that can automate the task of assignment of labels can include an electrical element, a microelectronic circuit associated with the electrical element, and an acquisition system. The microelectronic circuit can transmit a sequence comprising a label corresponding to the electrical element. The acquisition system can assign the label corresponding to the electrical element to a recording channel after decoding the sequence.

18 Claims, 5 Drawing Sheets

(56) References Cited

U.S. PATENT DOCUMENTS

| | | |
|---|---|---|
| 2010/0327051 A1 | 12/2010 | Lyon et al. |
| 2012/0203131 A1 | 8/2012 | DiLorenzo |
| 2014/0172057 A1 | 6/2014 | Orinski |
| 2014/0341456 A1 | 11/2014 | Rodriguez et al. |

* cited by examiner

SYSTEMS AND METHODS FOR AUTOMATED ELECTRICAL ELEMENT ADDRESSING

CROSS-REFERENCE TO RELATED APPLICATIONS

This application claims the benefit of U.S. Provisional Application No. 62/245,449, filed Oct. 23, 2015, entitled SYSTEMS AND METHODS FOR AUTOMATED ELECTRODE ASSIGNMENT, which is incorporated herein by reference in its entirety. This application also claims the benefit of U.S. Provisional Patent Application No. 62/337,938, filed May 18, 2016, entitled SYSTEMS AND METHODS FOR AUTOMATED ELECTRODE ASSIGNMENT, which is incorporated herein by reference in its entirety.

TECHNICAL FIELD

The present disclosure relates generally to electrical element addressing and more specifically to systems and methods for automated electrical element addressing.

BACKGROUND

Advances in electrode engineering have made it possible to simultaneously record data from hundreds of electrodes at the same time. However, a user must manually assign each of these electrodes to a certain recording channel location. Accordingly, the process of addressing these electrodes assigned to certain recording channel locations is quite cumbersome and time consuming. Additionally, in many situations, it may be useful to address other electrical elements, but manual addressing of these electrical elements can be difficult and time prohibitive.

SUMMARY

The present disclosure relates generally to electrical element addressing and more specifically to systems and methods for automated electrical element addressing. The automated addressing is far less cumbersome and requires less time than traditional manual addressing.

In one aspect, the present disclosure includes a method for automated electrical element addressing. A microcircuit associated with an electrical element can encode a sequence with a label corresponding to the electrical element. The microcircuit can transmit the sequence to an acquisition system, which can decode the sequence to determine the label corresponding to the electrical element. The acquisition system can assign the label corresponding to the contact to a recording channel.

In another aspect, the present disclosure includes a system that facilitates automated electrical element addressing. The system can include an electrical element, a microelectronic circuit, and an acquisition system. The microelectronic circuit can be associated with the electrical element and can transmit a sequence comprising a label corresponding to the electrical element to the acquisition system. The acquisition system can assign the label to a recording channel after decoding the sequence.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "electrical element" can refer to any device used within an electronic system that requires addressing. Examples of electrical elements can include electrodes, one or more contacts within the electrode, cables, and the like. The terms "electrical element" and "electrical component" can be used interchangeably herein. In some instances, the electrical element can be "addressable" (generally able to sell address) or "non-addressable" (generally unable to self-address without the presence of an adaptor insert placed serially inline with the electrical element).

As used herein, the term "electrode" can refer to a device that includes a conductor that can be used to establish electrical contact with a portion of a patient's body. The electrical contact can be used for recording, stimulating, and/or ablating. Electrodes can be constructed of different materials, in different shapes, or different sizes.

As used herein, the term "contact" can refer to a conductor that can establish the electrical contact with the portion of a patient's body. The contact can be made of one of a plurality of interface materials. In a multi-contact electrode, the one or more contacts can be made in different shapes and sizes. In some instances, the electrode can itself provide one or more conductors (e.g., the electrode can be made of a conductive material and covered by an insulating material except at the position of the contacts). In other instances, the electrode can provide an attachment means for the one or more contacts.

As used herein, the term "assignment" can refer to a process by which electrical elements are assigned to various recording channels using labels to distinguish between the electrical elements and/or to identify a recording channel or location associated with the electrical element. The terms "label" and "address" can be used interchangeably herein.

As used herein, the term "automated" can refer to something that occurs automatically with minimal human interaction. In other words, an automated process can occur virtually entirely by machine with the only human interaction being inputs to the machine.

As used herein, the term "microelectronic circuit" can refer to an electronic circuit consisting of miniaturized components. On example of a microcircuit is an integrated circuit, in which a number of permanently connected components are contained in one small chip of semiconducting material.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to electrical element (e.g., electrodes, electrode contacts, cables, and the like) addressing and more specifically to systems and methods for automated electrical element addressing. Currently, addressing is a timely process done manually by technicians, posing a risk of systemic error. The systems and methods described herein can automate the process by making electrical elements self-addressable. By automating the addressing process, the systems and methods of the present disclosure save time (e.g., roughly two hours) and reduce the possibility of systematic errors. The self-addressable elements, in some instances, must be powered on to supply location information. However, in other instances, the electrical elements need not be powered on—or even powered at all—to be self-addressable.

The ability to have self-addressable electrodes in the clinical arena will reduce costs and also reduce the risk of misconnections, which can result in significant patient risks. By automating the process of labeling of electrodes, the systems and methods of the present disclosure save time (e.g., roughly two hours) and reduce the possibility of systematic errors. The automated process is especially usefully as the number of electrode contacts that can be recorded from steadily increases. For example, this automated process can be used in EMG, EEG, cortical and depth micro arrays, intracranial eCoG or SEEG, basic biomedical science applications, which each simultaneously record from hundreds of electrodes.

The systems and methods described herein are not limited to the medical field. Indeed, the systems and methods can include entirely passive components, so uses span far beyond the medical field to perform the labeling functionality, in which, a different encoding scheme can include the introduction of a frequency or a combination of frequencies into the active signal, which could then be used as a carrier for the addressing signal and used for electrode, cable, or device identification. The passive circuitry could be built into the connector, the receptacle, or placed on the device. For example, the systems and methods can be used for labeling aircraft wiring, router box connectivity, residential industrial wiring, automotive wiring, and the like.

III. Systems

Figure 1:
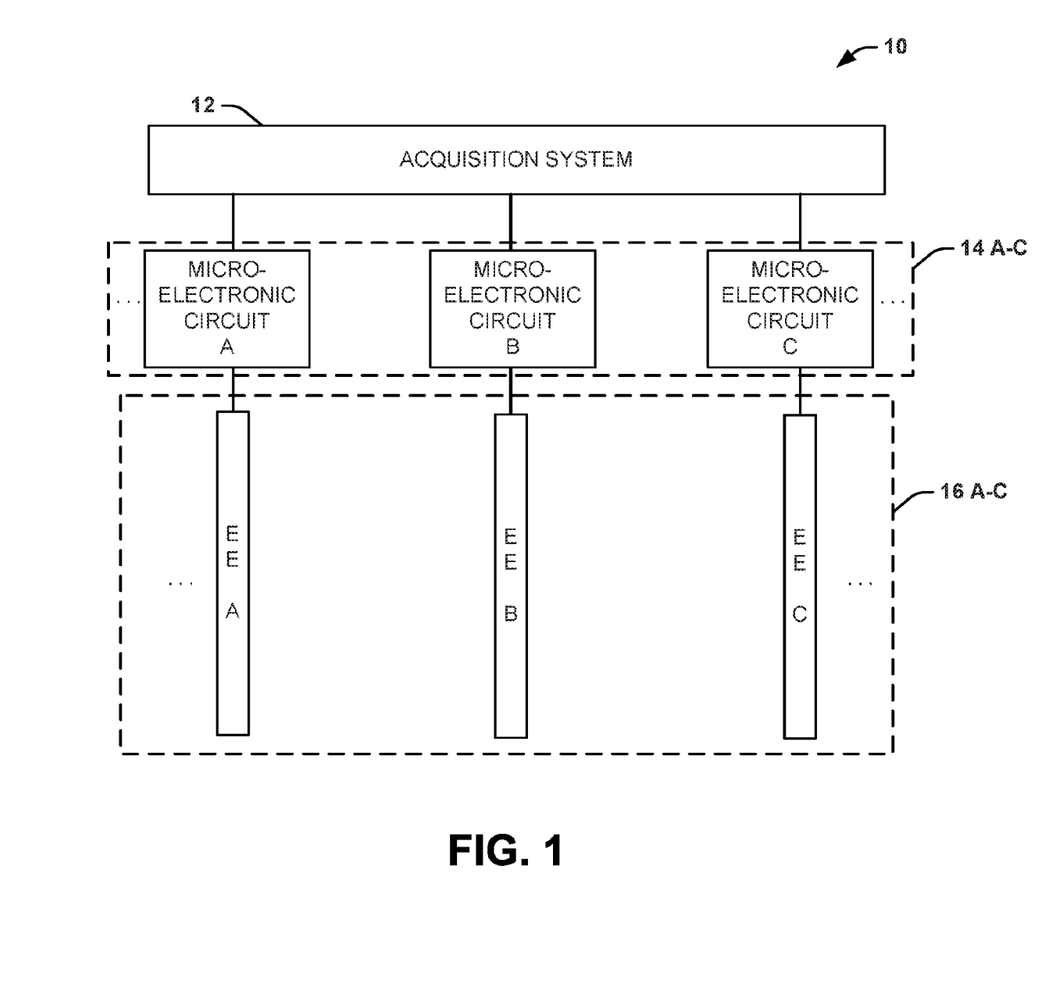
FIG. 1 is diagram of a system that can be used for automated electrical element assignment in accordance with an aspect of the present disclosure.

One aspect of the present disclosure can include a system 10 that facilitates automated electrical element addressing, as shown in FIG. 1. The electrical element addressing can involve the self-assignment of labels associated with electrical elements (EE) 16 A-C to recording channels in an acquisition system 12. The acquisition system 12 can be linked to a plurality of microelectronic circuits 14 A-C, which are each associated with a respective electrical element (EE) 16 A-C to facilitate the self-assignment. The microelectronic circuits 14 A-C can receive power to facilitate the self-assignment. However, in some instances, the self-assignment does not require power to be received by the microelectronic circuits 14 A-C.

The electrical elements (EE) 16 A-C can be electrodes, electrode contacts, wires, or other components. Although three electrical elements (EE) 16 A-C are illustrated in FIG. 1, it will be understood that there can be any number of electrical elements greater than two. Additionally, each of the illustrated electrical elements (EE) 16 A-C can have one or more associated electrical elements (e.g., each electrical element illustrated can be an electrode associated with a plurality of electrode contacts). For example, the electrical elements 16 A-C can include electrodes that can be can be used in medical tests that record simultaneously from hundreds of electrodes, including: EMG, EEG, tests using cortical and depth microarrays, intracranial eCoG, intracranial SEEG, and the like. As another example, the electrical elements 16 A-C can be used in areas beyond the medical field, including aircraft wiring, router box connectivity, residential industrial wiring, automotive wiring, and the like.

One or more of the electrical elements 16 A-C can be linked to the microelectronic circuits 14 A-C. Similarly, although three microelectronic circuits 14 A-C are illustrated in FIG. 1, each associated with a single electrical element (EE) 16 A-C, it will be understood that there can be any number of microelectronic circuits 14 A-C greater than one can be present in the system 10. In some examples, the microelectronic circuit 14 A, for example, can be associated with a single electrical element (EE) A for example. In other examples, the microelectronic circuit 14 B, for example, can be associated with one electrical element (EE) 16 B, for example, but the electrical element (EE) 16 B can be associated with a plurality of contacts. Accordingly, one microelectronic circuit 14 B can be associated with a plurality of electrical contacts associated with a single electrical element (EE) 16 B. As a further example, one microelectronic circuit 14 C, for example, can be associated with a plurality of electrical elements if electrical element 16 C included a plurality of electrical elements.

In some instances, the microelectronic circuits 14 A-C can require power to accomplish the addressing. For example, the microelectronic circuits 14 A-C can receive power either internally (e.g., from a small battery on or the microcircuit itself) or externally (e.g., from an output of the acquisition system 12, such as a USB or from an acquisition board). However, the electrical elements 16 A-C are often that are not powered, so the microelectronic circuit 14 A-C would benefit from not being powered.

Figure 2:
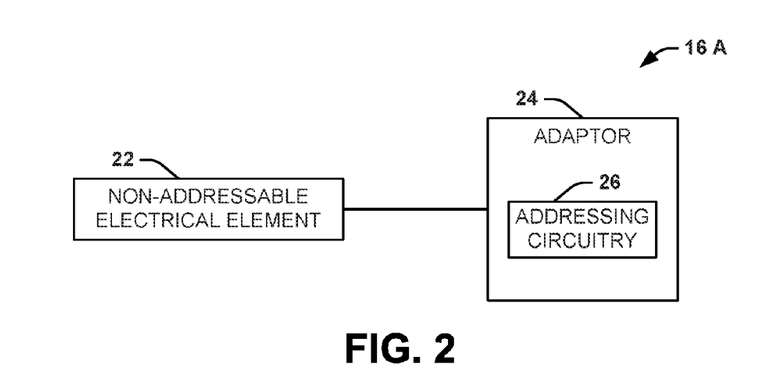
FIG. 2 is a diagram of an example of a non-addressable electrical element that can be used by the system in FIG. 1.

For example, electrical element (EE) 16A can be a non-addressable (not powered) electrical element 22, as shown in FIG. 2. A distal end of the non-addressable electrical element 22 can be linked serially inline to an adaptor 24 (the adaptor 24 can be associated with a single non-addressable electrical element 22 or a plurality of non-addressable electrical elements). The adaptor 24 can be an insert that includes addressing circuitry 26. In some instances, the adaptor 24 and/or the addressing circuitry 26 can be part of the microelectronic circuit 14 A. In other instances, the adaptor 24 and/or the addressing circuitry 26 can be distinct from the microelectronic circuit 14 A. Notably, the adaptor 24 can make the non-addressable electrical element 22 addressable without requiring the electrical element 22 to be powered.

The adaptor 24 can include one or more data connections to the microelectronic circuit 14 A and/or the acquisition system 12. For example, the adaptor 24 can receive a control signal through a first connection and transmit a source signal through a second connection. The adaptor 24 can also be connected to a ground of the microelectronic circuit 14 A and/or the acquisition system 12. In some instances, the adaptor 24 can also be connected to a source device (e.g., device controller, a user interface, or the like) to receive a source signal. The adaptor 24 can also include a connection that enables a power source to control onboard electronics of the adaptor 24.

Figure 3:
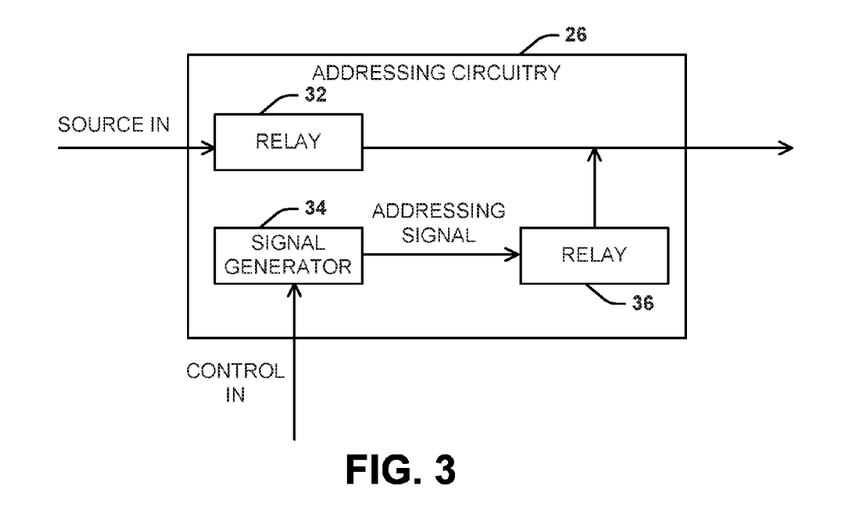
FIG. 3 is a diagram of the example addressing circuitry in FIG. 2.

The adaptor 24 can include addressing circuitry 26 that can facilitate the self-addressing of the non-addressable electrical element 22. The addressing circuitry 26 can transmit an addressing signal to the microelectronic circuit 14 A and/or the acquisition system 12. In some instances, the addressing circuitry 26 can transmit the addressing signal to the microelectronic circuit 14 A to correlate the non-addressable electrical element 22, to the appropriate recording channel. The microelectronic circuit 14 A and/or the acquisition system 12, As shown in FIG. 3, the addressing circuitry 26 can include two relay switches 32, 36 and a signal generator 34. The relay switch 32 can normally allow a line signal (SOURCE IN) to pass. The signal generator 34 can generate an addressing signal, which can include a specific label for a non-addressable electrical element 22, in response to a control signal input (CONTROL IN) from the microelectronic circuit 14 A and/or the acquisition system 12. When the relay switch 32 allows the line signal to pass, the relay switch 36 restricts the addressing signal from passing. For example, upon receiving the control signal, signal generator 34 can instruct the relay switch 32 to restrict passage of the line signal so that the addressing signal can be transmitted through relay switch 36.

In some instances, the addressing circuitry does not use the switches 32 and 36 and can instead write the addressing signal over the line signal. For example, the addressing signals can be a high frequency component (or other component different from the line signal), while the line signal can have a lower frequency. The high frequency signal can overlie the high frequency signal so that frequency components of the high frequency signal can be extracted to correspond to the labels.

The adaptor 24 of FIG. 2 can encode the addressing signal and transmit the addressing signal to the microelectronic circuit 14 A and/or the acquisition system 12. In passing to the microelectronic circuit 14 A and/or the acquisition system 12, the addressing signal can pass through a decoder, which can be included with the microelectronic circuit 14, the acquisition system 12, a standalone device, or a unique circuit element. The addressing signal or the processed addressing signal can pass to the microelectronic circuit 14 A as an analog signal or a digital signal. For example, the decoder can include decoding logic to isolate the label from the addressing signal, determine the label, and pass a digital signal that includes the label to the microelectronic circuit 14 A and/or the acquisition system 12. For example, the standalone device can be a computer, a smartphone, a tablet computing device, or any other device that can read the code directly offline.

Figure 4:
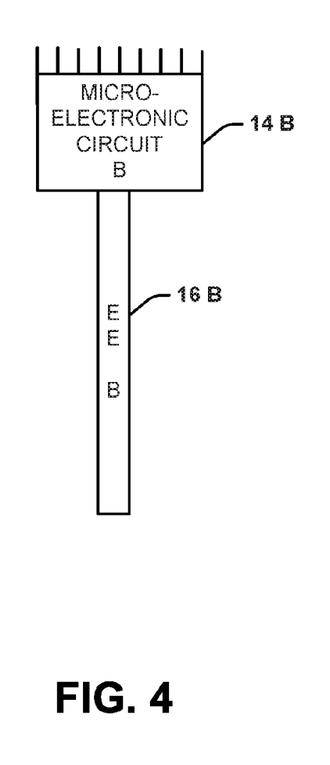
FIGS. 4 and 5 are diagrams showing different configurations of an electrical element and microcircuit pair that can be used by the system in FIG. 1.
Figure 5:
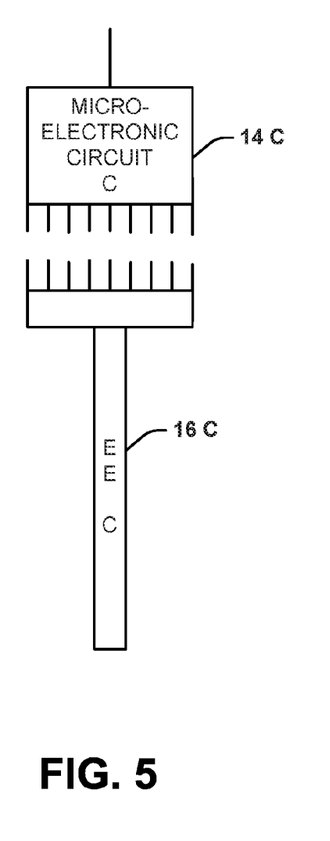

Referring again to FIG. 1, the microelectronic circuits 14 A-C can have alternate configurations. In the example shown in FIG. 4, a microelectronic circuit 14 B can be placed in physical contact with its respective electrical element (EE) 16 B. In another example, shown in FIG. 5, the microelectronic circuit 14 C can be placed in physical contact with (or located within) a connector that connects the electrical element (EE) 16 C to the acquisition system 12. In this example, the microelectronic circuit 16 C can be located entirely within the connector or can be located partially within the connector (with the rest of the microelectronic circuit 14 C located on the electrical element 16 C).

The microelectronic circuit 14 A-C of FIG. 1 and/or the adaptor 24 of FIG. 2 can encode and transmit an addressing signal. In some instances, the addressing signal can include a start sequence, a label sequence, and a stop sequence. The addressing signal can include a pulse sequence with the different parts identifiable based on varying frequency, amplitude, and/or interpulse interval.

Figure 6:
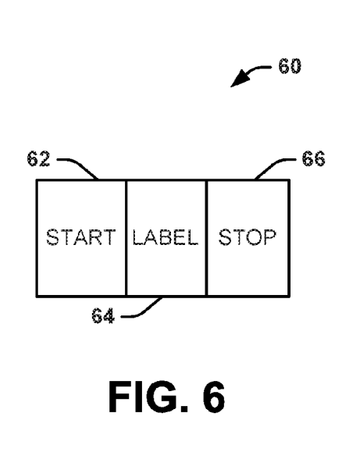
FIG. 6 is a diagram of a sequence that can be used for the automated electrical element assignment of FIG. 1.

An example of the sequence 60 is shown in FIG. 6. The sequence 60 can include a start 62 portion, a label 64 portion, and a stop 66 portion. The start 62 portion and the stop 66 portion can be made up of a series of pulses with small inter-pulse intervals. Following the start 62 portion, a series of pulses (with longer inter-pulse intervals) can be used to describe information, including the label, relative to at least one of the electrical elements 16 A-C. As an example, for an electrode with a plurality of contacts, the sequence can be a sequence of series pulses that can describe the labels of each contact on the electrode. The stop 66 portion of short inter-pulse intervals can be used to inform the acquisition system 12 that the labeling 64 portion has completed the label for the electrical element. In addition, the amplitude may also be used along or in combination with sequences for labeling purposes.

Referring again to FIG. 1, the acquisition system 12 can decode the sequence to retrieve the label for one or more of the electrical elements 16 A-C. After decoding the sequence to retrieve the label, the acquisition system 12 can associate a recording channel with the label to indicate that the data collected at the recording channel is from the electrical element 16 A-C at a specific location. The association of the label with the recording channel is automatically conducted by the acquisition system 12 and/or the microelectronic circuit 14 A-C.

The label can include both positive and negative values, with the positive values represented by a 1 and the negative values represented by a 0. The acquisition system 12 can interpret the label based on a binary encoding scheme of known word length. For example, an 8-bit word can consist of a sequence of 1 or 0 values eight pulses long, providing 256 combinations per word ($2^8$ combinations). As another example, a 10-bit word can consist of a sequence of 1 or 0 values ten pulses long, providing 1024 combinations per words ($2^{10}$ combinations). The amplitude (or high) of a pulse can be used in addition to and/or as an alternative to the pulse sequence alone in the label.

The acquisition system 12 can create an interface with the microelectronic circuits 14 A-C. In some instances, the interface can include a user input modality that can enable a user to reassign the electrode labeling scheme. However, the user input modality can be associated with the microelectronic circuit 14 A-C and/or the In other instances, the interface can allow the acquisition system 12 to query labels, to reassign labels, and to decode transmitted labels.

A component of the system (at least one of the microelectronic circuit 14 A-C, the acquisition system 12, or an additional element that is not illustrated) can also include software that is stored in a non-transitory memory and executed by a processor to perform different functions. The functions can include configuring connected input lines and configure channels for use in the labeling. In other words, the software can link one of the input lines with a respective channel and associate the label with the appropriate input line and channel. For example, the label can be stored in a lookup table (or registry) with the appropriate input corresponding to one electrical element 16 A-C and the appropriate recording channel. The addresses in the lookup table are editable. For example, edits to at least one of the labels stored in the lookup table can be received and of at the at least one of the addresses can be replaced with the edits. The edits can be stored in the lookup table (e.g., overwriting the original address).

In some instances, the lookup table can be programmed remotely. For example, the programming can be done through a hand-held or mobile device that can scan (or otherwise read) a label printed on the electrical element 16 A-C. Once scanned, an installation technician can define a source (e.g., the electrical element 16 A-C and/or the associated channel) and other control information needed for the specific electrical element 16 A-C scanned.

In other instances, the lookup table can be made available to vendors. For example, the acquisition system 12 can include an addressing controller, which interacts with the microelectronic circuits 14 A-C and/or the adaptor 24, and a vendor specific device controller. Specifically, a vendor can register encoding circuitry located on their equipment that makes use of the addressing controller. In this case, the vendor can register the encoding address on each output/input of their equipment that can automatically update the lookup table when attached. The codes will be individually registered and unique such that the microelectronic circuit 14 A-C and/or the acquisition system 12 will use a lookup table designed by the vendor and the encoder can be built into a connection of the device controller to the addressing controller.

In some instances, the software can configure outputs and inputs to connectors attached to a device controller designed for specific vendor applications of the electrical elements 16 A-D. In other instances, users or vendors can use the software to build applications that utilize one or more of the labels directly to control the associated electrical element 16 A-C. For example, the addressing controller can receive inputs from a user interface to control or utilize one or more of the electrical elements 16 A-C.

IV. Methods

Figure 7:
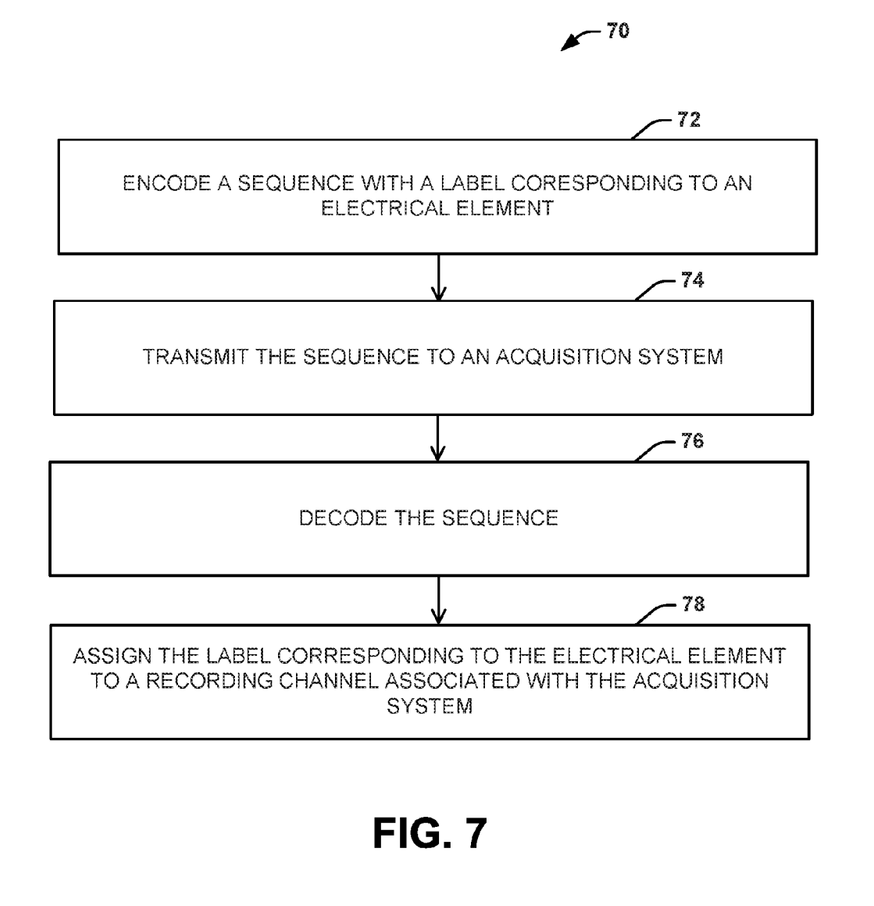
FIG. 7 is a process flow diagram illustrating a method for automated electrical element assignment in accordance with another aspect of the present disclosure.
Figure 8:
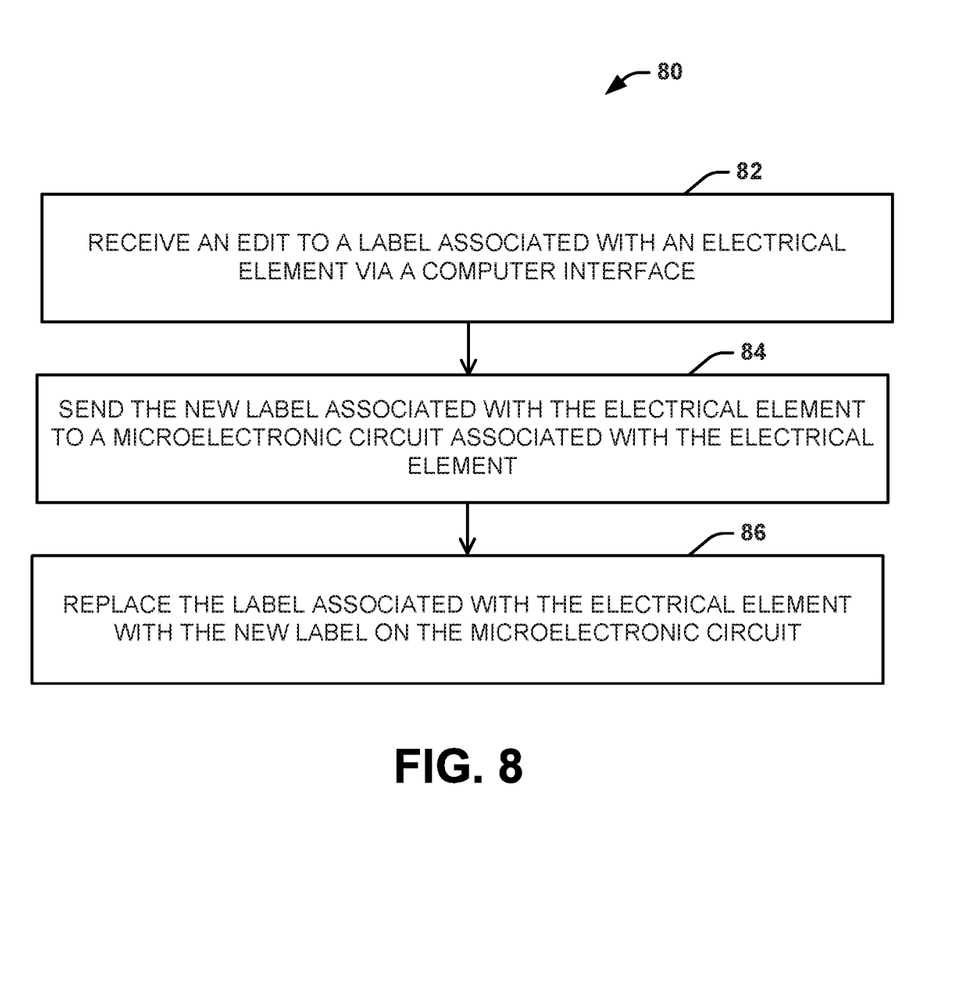
FIG. 8 is a process flow diagram illustrating a method for editing a label of an electrical element after assignment.

Another aspect of the present disclosure can include a method 70 for automated electrical element assignment, as shown in FIG. 7. FIG. 8 shows a method 80 that is an extension of method 70, in which the label of the electrical element can be edited. As an example, the methods 70 and 80 can employ the system 10, as shown in FIG. 1, to facilitate the autonomous addressing of electrical elements, including electrodes, electrode contacts, different types of wiring, or the like. As described above, the methods 70 and 80 need not be directed to electrodes, and can be directed to any different type of wiring. Example applications where the autonomous addressing can be used include neurological procedures, industrial cabling, residential cabling, automotive cabling, aircraft cabling, internet/Ethernet cabling, and the like.

The methods 70 and 80 are illustrated as process flow diagrams with flowchart illustrations. For purposes of simplicity, the methods 70 and 80 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 70 and 80.

FIG. 7 illustrates a method 70 for automated electrical element addressing. In some instances, the automated addressing can include self-assignment of address labels to electrical elements. For example, the electrical elements can include electrodes that can be can be used in medical tests that record simultaneously from hundreds of electrodes, including: EMG, EEG, tests using cortical and depth microarrays, intracranial eCoG, intracranial SEEG, and the like. The method 70 can be an entirely passive system that can be used in areas beyond the medical field, including aircraft wiring, router box connectivity, residential industrial wiring, automotive wiring, and the like (e.g., in FIG. 1, the electrical elements (EE) 16 A-C can be electrodes, electrode contacts, wires or other components).

As illustrated in FIG. 1, microelectronic circuits 14 A-C can be associated with electrical elements 16 A-C. In some instances, at least one of the electrical elements 16 A-C can be self-addressable. In other instances, at least one of the electrical elements A-C can be non-addressable (in which case the microelectronic circuit includes components shown in FIGS. 2 and 3). The microelectronic circuits 14 A-C can be placed serially inline with respective electrical elements (EE) 16 A-C (e.g., one microelectronic circuit serially inline with a plurality of electrical elements, one microelectronic circuit for one electrical element, or any other configuration in which the microelectronic circuit is serially in line with the respective electrical elements).

At 72, an addressing signal can be created (by the microelectronic circuit 14 A-C) by encoding a sequence with a label corresponding to an electrical element (one of electrical element (EE) 16 A-C). The sequence can be a sequence of series pulses that can describe the labels of each electrical element serially inline with the microelectronic circuit. For example, the sequence can include a start portion, a label portion, and a stop portion. The start portion and the stop portion can be made up of a series of pulses with small inter-pulse intervals, while the label portion can include a series of pulses (with longer inter-pulse intervals) can be used to describe information, including the label, relative to at least one of the contacts on the electrode. The stop portion of short inter-pulse intervals can be used to inform the acquisition system 12 that the labeling portion has completed the label for the electrical element.

At 74, the sequence can be transmitted to the acquisition system, and, at 76, the sequence can be decoded so that the label can be retrieved. The decoding can be done by a component of the acquisition system, a component of the microelectronic circuit, and/or a standalone component. The decoded signal can be used by software to set labels for the electrical elements. For example, the decoding can be based on an interpretation of the label based on an interpretation of the label based on a binary encoding scheme of known word length. For example, an 8-bit word can consist of a sequence of 1 or 0 values eight pulses long, providing 256 combinations per word ($2^8$ combinations). As another example, a 10-bit word can consist of a sequence of 1 or 0 values ten pulses long, providing 1024 combinations per words ($2^{10}$ combinations). The high of a pulse can be used in addition to or as an alternative to the pulse sequence.

At 78, the label (based on the decoded sequence) can be assigned to a recording channel of the acquisition system linked to the respective electrical element. The assignment can be accomplished automatically by the microelectronic circuit, the assignment system, and/or an external device. In some instances, the label representing electrical element-recording channel linkage can be stored in a look-up table (which can be stored on the microelectronic circuits, on the acquisition system, and/or on an external device). The linkage indicates that the data collected at the recording channel is from the specific electrical element at a specific location.

A user can edit or change the label and/or the linkage via a user interface with the microelectronic circuits. In other instances, the user interface can be associated with the acquisition system. The microelectronic circuits can be entirely passive and/or include passive components, allowing the identification of electrodes and other generalized wires in other applications.

A method 80 for changing the label is shown in FIG. 8. The editing or changing of the label can be made consistent between the channel and the microelectronic circuit automatically. This can be due to a two-way interface that is established between the respective microelectronic circuit (e.g., microelectronic circuit 14 A-C) and the acquisition system (e.g., acquisition system 12).

At 82, an edit can be received via a computer interface. For example, the edit can be from a user. The edit can include a new label for a respective electrical element. In other examples, the edit can be automatic from the assignment system. At 84, the new label can be sent to the respective microelectronic circuit. At 86, the label can be replaced with the new label on the respective microelectronic circuit. The label can also be replaced on the channel within the acquisition system to ensure consistency.

From the above description, those skilled in the art will perceive improvements, changes and modifications. Such improvements, changes and modifications are within the skill of one in the art and are intended to be covered by the appended claims.

What is claimed is:
1. A method comprising:
 encoding, by a microcircuit associated with an electrical element, a sequence with a label corresponding to the electrical element;
 transmitting, by the microcircuit, the sequence to an acquisition system;
 decoding, by the acquisition system, the sequence to determine the label corresponding to the electrical element; and
 assigning, by the acquisition system, the label corresponding to the electrical element to a recording channel,
 wherein the electrical element comprises an addressable electrode contact, an addressable electrode comprising a plurality of electrode contacts, or a non-addressable electrical element.

2. The method of claim 1 further comprising placing an adaptor comprising the microcircuit serially inline with the electrical element.

3. The method of claim 1, wherein the sequence comprises a start, a label identifier, and a stop, and
 wherein the start sequence, the address sequence, and the stop sequence are identifiable due to at least one of interpulse intervals, amplitudes, and frequencies.

4. The method of claim 3, wherein the label identifier comprises a binary sequence of positive and negative values according to an encoding scheme.

5. The method of claim 3, wherein at least one of the start and the stop comprises a series of pulses with small inter-pulse intervals.

6. The method of claim 5, wherein the label identifier comprises a series of pulses with larger inter-pulse intervals or pulse heights than the at least one of the start and the stop, and
 wherein the series of pulses of the label identifier describes information relative to a specific electrode.

7. The method of claim 1, further comprising permitting, by the acquisition system, the label to be edited.

8. The method of claim 7, wherein the label is edited by:
 receiving, via a computer interface, an input comprising an edit to the label;
 sending, by the acquisition system, the edited label to the microcircuit; and
 replacing, by the microcircuit, the label with the edited label,
 wherein the edited label replaces the label stored on the microcircuit.

9. The method of claim 1, wherein the microcircuit physically contacts the electrical element or the microcircuit physically contacts a connector between the acquisition system and the electrical element.

10. A system comprising:
 a non-addressable electrical element associated with an adaptor insert comprising addressing circuitry and a controller;
 a microelectronic circuit associated with the non-addressable electrical element to transmit a sequence comprising a label corresponding to the non-addressable electrical element; and
 an acquisition system to assign the label to a recording channel after decoding the sequence.

11. The system of claim 10, wherein the acquisition system is designed for a vendor application of the non-addressable electrical element.

12. The system of claim 10, wherein the addressing circuitry comprises:
 a first relay to allow a line signal to pass;
 a signal generator to provide the addressing signal in response to the input from the controller; and
 a second relay to allow the addressing signal to pass,
 wherein the addressing signal is related to the label.

13. A system comprising:
 an electrical element;
 a microelectronic circuit associated with the electrical element to transmit a sequence comprising a label corresponding to the electrical element; and
 an acquisition system to assign the label to a recording channel after decoding the sequence,
 wherein the assigned label and recording channel are stored in an editable lookup table.

14. The system of claim 13, further comprising at least two electrical elements, each associated with a unique microelectronic circuit.

15. The system of claim 13, further comprising an interface to the microelectronic circuit or the acquisition system that enables a user to reassign an electrode labeling scheme to the electrode.

16. The system of claim 13, wherein the electrical element comprises an electrode,
wherein the electrode comprises a plurality of contacts, each with a unique label.

17. The system of claim 13, wherein the acquisition system comprises a decoder to decode the sequence to determine the label corresponding to the electrical element.

18. The system of claim 13, electrical element comprises an addressable electrode contact, an addressable electrode comprising a plurality of electrode contacts, or a non-addressable electrical element.

* * * * *